United States Patent [19]

Baglioni

[11] Patent Number: 4,578,481

[45] Date of Patent: Mar. 25, 1986

[54] PYRROLACETIC AMIDES HAVING ANTIINFLAMMATORY ACTIVITY

[75] Inventor: Alessandro Baglioni, Rome, Italy

[73] Assignees: Sigma-Tau Industrie Farmaceutiche Riunite S.p.A., Rome; Medosan Industrie Biochimie Riunite S.p.A., Albano Laziale, both of Italy

[21] Appl. No.: 728,758

[22] Filed: Apr. 30, 1985

Related U.S. Application Data

[62] Division of Ser. No. 700,059, Feb. 11, 1985, which is a division of Ser. No. 467,308, Feb. 17, 1983, abandoned.

[30] Foreign Application Priority Data

Feb. 26, 1982 [IT] Italy ............................. 47881 A/82

[51] Int. Cl.$^4$ ......................................... C07D 207/323
[52] U.S. Cl. ................................... 548/539; 544/141; 544/372; 546/281
[58] Field of Search ........................................ 548/539

[56] References Cited

U.S. PATENT DOCUMENTS

| | | | |
|---|---|---|---|
| 3,950,012 | 4/1976 | Carson | 548/539 X |
| 4,070,368 | 1/1978 | Carson | 548/539 X |
| 4,200,645 | 4/1980 | Goudie | 548/539 X |
| 4,379,793 | 4/1983 | Badia | 514/423 |
| 4,396,626 | 8/1983 | Ward et al. | 514/274 |
| 4,434,175 | 2/1984 | Doherty et al. | 514/423 |
| 4,521,538 | 6/1985 | Baglioni | 514/423 |

FOREIGN PATENT DOCUMENTS

| | | | |
|---|---|---|---|
| 0051981 | 5/1982 | European Pat. Off. | 548/539 |
| 3306006 | 9/1983 | Fed. Rep. of Germany | 548/539 |
| 55-24141 | 2/1980 | Japan | 548/539 |
| 2098989A | 12/1982 | United Kingdom | 548/539 |
| 2115417A | 9/1983 | United Kingdom | 548/539 |
| 2134111A | 8/1984 | United Kingdom | 548/539 |

OTHER PUBLICATIONS

Abstract of Japan Application, 0144256, Sep. 6, 1982.

Primary Examiner—Joseph Paul Brust
Attorney, Agent, or Firm—Ladas & Parry

[57] ABSTRACT

N-monosubstituted and N,N-disubstituted amides of the 1-methyl-5-p-toluoylpyrrole-2-acetic acid, which are active as antiinflammatory, analgesic, antipyretic, antisecretive and antitussive agents, are disclosed.

These amides are prepared by reacting an amine with an activated derivative of the 1-methyl-5-p-toluoylpyrrole-2-acetic acid of formula

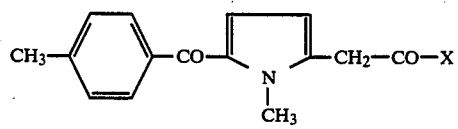

wherein X is an activating group suitable for promoting the formation of an amide bond.

1 Claim, No Drawings

PYRROLACETIC AMIDES HAVING ANTIINFLAMMATORY ACTIVITY

This is a divisional of co-pending application Ser. No. 700,059, filed on Feb. 11, 1985, which latter file is in turn a divisional of Ser. No. 467,308, filed on Feb. 17, 1983, now abandoned.

The present invention relates to a novel class of amides of the 1-methyl-5-p-toluoylpyrrole-2-acetic acid, which possess valuable antiinflammatory, analgesic, antipyretic, antisecretive and antitussive properties. The present invention also relates to a process for the preparation of such amides and to pharmaceutical compositions containing same.

More specifically, the present invention relates to the amides of the 1-methyl-5-p-toluoylpyrrole-2-acetic acid having general formula (I):

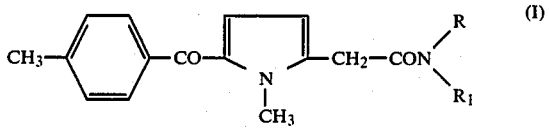

wherein:
R is H, or
an unsubstituted alkyl radical having from 1 to 3 carbon atoms, or
an alkyl radical having from 1 to 3 carbon atoms substituted with OH, SH or $NH_2$ groups, or
is such to form with the illustrated nitrogen atom and with $R_1$ a saturated heterocyclic ring having formula

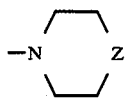

wherein Z is O, S, $NR_2$ or $(CH_2)_n$ wherein $R_2$ is H, $CH_3$, $C_2H_5$, $CH_2CH_2OH$, $CH_2COOH$ or $CH_2CH_2NH_2$ and n is an integer comprised between 0 and 3, and (a) if R is H
$R_1$ is an unsubstituted alkyl radical having from 1 to 3 carbon atoms, or
an alkyl radical having from 1 to 3 carbon atoms substituted with $COOR_3$, OH, $NH_2$, SH or Cl groups, wherein $R_3$ is H, $CH_3$, $C_2H_5$, cycloalkyl having from 4 to 6 carbon atoms, phenyl, alkoxy-substituted phenyl, the alkoxy group having from 1 to 3 carbon atoms or alkylphenyl, or
an alkylamino radical having from 1 to 3 carbon atoms substituted with a $COR_4$ group wherein $R_4$ is

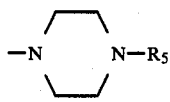

wherein $R_5$ is an alkyl radical having from 1 to 3 carbon atoms, or
an unsubstituted cycloalkyl radical having from 4 to 6 carbon atoms, or a cycloalkyl radical having from 4 to 6 carbon atoms, substituted with alkyl groups having from 1 to 3 carbon atoms or hydroxyl groups, or a phenyl radical substituted with one or more alkyl radicals having from 1 to 3 carbon atoms, hydroxy or mercapto groups or the esters thereof with saturated organic acids having from 2 to 4 carbon atoms; carboxyl groups or the esters thereof with alcohols having from 1 to 3 carbon atoms, halogens or $NO_2$, $NH_2$ or $CF_3$ groups, or a 5-membered or 6-membered, unsaturated or aromatic heterocyclic radical, containing either one heteroatom or more heteroatoms, which are equal or different from each other, selected among nitrogen, sulfur and oxygen, which is unsubstituted or substituted with $COOCH_3$, $CH_3$, $OCH_3Cl$ or phenyl groups;

(b) if R is an unsubstituted alkyl radical or an alkyl radical substituted with OH, SH or $NH_2$ groups
$R_1$ is an unsubstituted alkyl radical having from 1 to 3 carbon atoms, or
an alkyl radical having from 1 to 3 carbon atoms substituted with OH, SH or $NH_2$ groups,
and to their pharmacologically acceptable salts.

Preferred, although non-limiting, examples of amides of general formula (I) are the following:

1-methyl-5-p-toluoylpyrrole-2-N-(cyclohexyl)acetamide;
1-methyl-5-p-toluoylpyrrole-2-acetamidoacetic acid;
1-methyl-5-p-toluoylpyrrole-2-acetamidoacetic acid ethyl ester;
1-methyl-5-p-toluoylpyrrole-2-acetamidoacetic acid guaiacyl ester;
1-methyl-5-p-toluoylpyrrole-2-N-(2-mercapto-1-ethyl)acetamide;
1-methyl-5-p-toluoylpyrrole-2-N-(1-carboxymethyl-2-mercapto-1-ethyl)acetamide;
1-methyl-5-p-toluoylpyrrole-2-N-(4-methyl-2-pyridyl)acetamide;
1-methyl-5-p-toluoylpyrrole-2-N-(4-carboxyethylphenyl)acetamide;
1-methyl-5-p-toluoylpyrrole-2-N-(4-carboxyphenyl)acetamide;
1-methyl-5-p-toluoylpyrrole-2-N-(4-hydroxyphenyl)acetamide;
1-methyl-5-p-toluoylpyrrole-2-N-(3-trifluoromethylphenyl)acetamide;
1-methyl-5-p-toluoylpyrrole-2-N-(3,5-dimethylphenyl)acetamide;
1-methyl-5-p-toluoylpyrrole-2-acetic acid-2[N-(4-methyl-1-piperazinyl)acetamide]hydrazide;
1-methyl-5-p-toluoylpyrrole-2-N,N'-(diethyl)acetamide;
1-methyl-5-p-toluoylpyrrole-2-N-[(4-methyl)-1-piperazinyl]acetamide; and
1-methyl-5-p-toluoylpyrrole-2-N-(4-morpholinyl)acetamide.

All the foregoing compounds are structurally related to 1-methyl-5-p-toluoylpyrrole-2-acetic acid (U.S. patent application Ser. No. 656,074, filed July 26, 1967, now abandoned, in the name of John Robert Carson), an antiinflammatory agent known with the nonproprietary name of TOLMETIN and used in therapy in the form of its sodium salt dihydrate (TOLMETIN $Na.2-H_2O$). TOLMETIN belongs to the class of the antiinflammatory agents having pyrrole structure, analogously to CLOPIRAC, (1-p-chlorophenyl-2,5-dimethylpyrrole-3-yl)acetic acid, and ZOMEPIRAC, 5-(4-chlorobenzoyl)-1,4-dimethylpyrrole-2-yl acetic acid.

These antiinflammatory agents provoke toxic effects on the gastrointestinal tract such as haemorrhage and peptic ulceration, because of the presence of the carboxyl group in their molecules.

In an endeavour to eliminate these toxic effects, there have been already studied derivatives of TOLMETIN wherein an ester group replaces the carboxyl group. However, these ester derivatives have turned out to be pro-drugs of TOLMETIN, insofar as the hydrolytic enzymes in vivo convert the ester back to the acid.

It has now been found that the amide derivatives of formula (I) according to this invention are unaffected by the hydrolytic action in vivo of the enzymes. These compounds possess an antiinflammatory activity of their own, such action being not provoked by the conversion of the amide back to the acid, i.e. they are not TOLMETIN pro-drugs. Moreover, they possess a more potent and longer lasting antiinflammatory activity than TOLMETIN. In addition, they also possess analgesic, antipyretic, antisecretive and antitussive properties which make them therapeutically effective agents.

The process for preparing the compounds of formula (I) comprises the following steps:

(a) reacting an amine of general formula $NHRR_1$ wherein R and $R_1$ have the previously defined meanings with an activated derivative of the 1-methyl-5-p-toluoylpyrrole-2-acetic acid of general formula

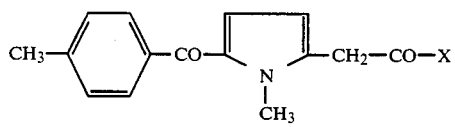

wherein X is an activating group suitable for promoting the formation of an amide bond with the previously specified amines, at a temperature comprised between about 0° C. and 35° C., in the presence of either aprotic or protic solvents depending on the nature of the activating group, and optionally, in case the product of step (a) contains the $COOR_3$ group, wherein $R_3$ has the previously specified meaning except that $R_3=H$.

(b) hydrolyzing the product of step (a), thus releasing the corresponding acid, and optionally (c) esterifying the acid of step (b) with a compound having formula $R_3OH$ wherein $R_3$ has the above specified meaning except $R_3=H$.

Suitable activated derivatives of formula

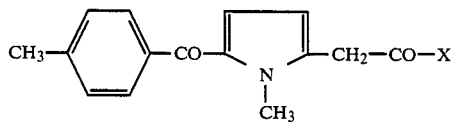

are those wherein X is selected from the group consisting of the halogen atoms (preferably chlorine), the $$-O-\underset{\underset{N-R_7}{\|}}{C}-NH-R_6$$

residue, wherein $R_6$ and $R_7$ are alkyl radicals having from 1 to 3 carbon atoms or cycloalkyl radicals having from 5 to 6 carbon atoms, preferably cyclohexyl, and the

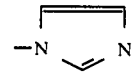

residue.

All these activated derivatives can be prepared by well-known procedures.

When X is halogen (e.g. chlorine), the corresponding activated derivative can be prepared by halogenating (e.g. chlorinating) 1-methyl-5-p-toluoylpyrrole-2-acetic acid.

When X is the $$-O-\underset{\underset{N-R_7}{\|}}{C}-NH-R_6$$

residue (preferably, $R_6=R_7=$cyclohexyl), the corresponding activated derivative is prepared by condensing 1-methyl-5-p-toluoylpyrrole-2-acetic acid with an N,N'-dialkylcarbodiimide (preferably, N,N'-dicyclohexylcarbodiimide). This condensation reaction can be suitably carried out in the presence of a catalyst, such as p-toluenesulfonic acid and 4-dimethylaminopyridine.

When X is the

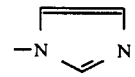

residue, the corresponding activate derivative is prepared by condensing 1-methyl-5-p-toluoylpyrrole-2-acetic acid with N,N'-carbonyldiimidazole. This condensation reaction can be suitably carried out in the presence of a catalyst, such as sodium or magnesium ethylate.

The amount of amine varies generally between 1 and 1.5, preferably 1.2, times the equivalent amount of the activated derivative. In the following table I there are illustrated some exemplificatory amines suitable for reaction with the activated derivative according to this invention.

TABLE I

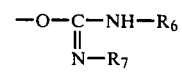

TABLE I-continued

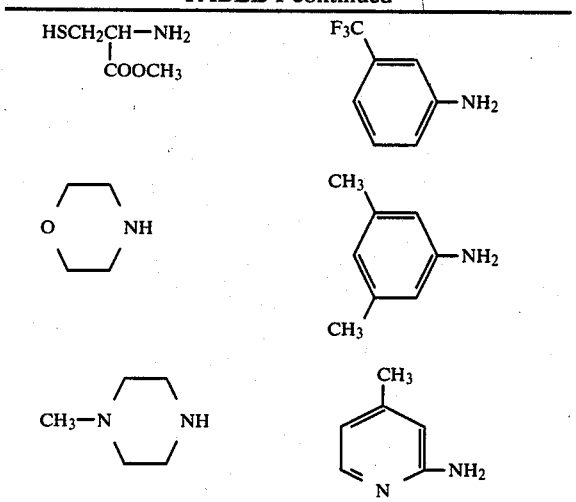

Step (a) of the process is generally carried out in a nonpolar environment, although water-dioxane and water-tetrahydrofuran mixtures can be employed when N,N'-dicyclohexylcarbodiimide is used as condensing agent, in the presence or absence of a catalyst. Preferred solvents are the following: dichloromethane, dichloroethane, tetrahydrofuran, dioxane, dimethyl-sulfoxide and N,N-dimethylformamide. The highest yields are obtained with anhydrous solvents and are comprised in the range of 50-90%. The average yield is about 70%. The reaction temperature is comprised between about 0° C. and 35° C., the optimum temperature being about 20° C. The reaction mixture is preferably kept under vigorous stirring, in an atmosphere of nitrogen or other inert gas, if required. The reactants are slowly added to each other in such a way as to keep the reaction temperature at its optimum value. The reaction is completed in a time period varying from about 15 minutes to about 6 hours, depending on the specific amine.

The further processing of the reaction mixtures is carried out in the usual ways by well-known separation techniques, such as filtration, chromatography on columns of silica gel, alumina (used as such or partly deactivated), or other inert materials.

The pharmacologically acceptable salts of the compounds of general formula (I) can be obtained by well-known procedures by reacting the acid or basic compounds of general formula (I) with, respectively, a pharmacologically acceptable, non toxic, base or acid. These pharmacologically acceptable, non toxic bases and acids are well-known to those skilled in the pharmacological art. The salts formed with the acid compounds are preferably the sodium, potassium, glucamine and diethanolamine salts. The salts formed with the basic compounds are preferably hydrochlorides, sulfates, salicilates, benzoates and pamoates.

The following non-limiting examples and the Tables II and III illustrate the preparation and chemico-physical characteristics of some of the compounds of the present invention.

EXAMPLE 1

Preparation of 1-methyl-5-p-toluoylpyrrole-2-acetamidoacetic acid ethyl ester (1-b, see Table II).

A solution of 3.4 grams (0.021 moles) of 1,1'-carbonyldiimidazole in 70 ml of anhydrous tetrahydrofuran was added under vigorous stirring and cooling on iced water in such a way as to maintain the temperature at about 20° C. to a solution of 4.6 grams (0.018 moles) of 1-methyl-5-p-toluoylpyrrole-2-acetic acid in 150 ml of anhydrous tetrahydrofuran (THF). The addition lasted about 30 minutes. Subsequently, the resulting mixture was left under vigorous stirring at 20° C. for 1 hour. Then to the mixture 3.2 grams (0.023 moles) of aminoacetic acid ethyl ester hydrochloride were added and the resulting suspension was kept under vigorous stirring while 3.2 ml (2.3 grams; 0.023 moles) of triethylamine dissolved in 20 ml of anhydrous THF were added dropwise to the suspension (the addition of this reactant can be omitted in those cases wherein the free amine is used in lieu of its hydrochloride). The mixture was kept under stirring at 20° C. for 3 hours, then the triethylamine hydrochloride which precipitated was filtered off and the clear solution thus obtained was evaporated under reduced pressure on a water bath at 55° C. The thick and oily residue which formed was dissolved in 200 ml of ethyl acetate and transferred into a separatory funnel. The organic solution was first washed with 1N NaOH (3×30 ml) in order to remove the unreacted 1-methyl-5-p-toluoylpyrrole-2-acetic acid, then with water (3×30 ml). Subsequently, the washings were continued with 1N HCl (3×30 ml) in order to remove the excess starting amine which did not react, and finally the organic solution was washed with a saturated solution of NaCl (3×30 ml) until neutrality was reached. The organic solution was dried by letting it stand for 12 hours on anhydrous sodium sulphate. After filtration the solvent was removed by evaporation under vacuum on a water bath at 50° C. A solid residue was thus obtained which, after crystallization from benzene-cyclohexane (1:1), gave 4.8 grams of a compound of formula:

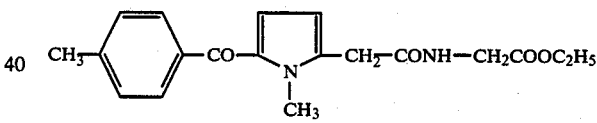

having the following chemico-physical characteristics:
Formula: $C_{19}H_{22}N_2O_4$.
Molecular weight: 342.38.
Melting point: 132°-133° C.
Yield: 78.7% of the theoretical value.
Solubility: soluble in the usual organic solvents.
Analysis: $C_{19}H_{22}N_2O_4$. Calculated %—C 66.65; H 6.48; N 8.18. Found %—C 66.47; H 6.40; N 7.90.
I.R. Spectrum (nujol): 3275 cm$^{-1}$ (amide NH); 1750, 1725, 1640 and 1620 cm$^{-1}$ (C=O ester, keto and amide groups).

EXAMPLE 2

Preparation of 1-methyl-5-p-toluoylpyrrole-2-acetamidoacetic acid (1-c; see Table II).

A mixture consisting of 4.45 grams (0.013 moles) of 1-methyl-5-p-toluoylpyrrole-2-acetamidoacetic acid ethyl ester (1-b), 50 ml of ethanol, 25 ml of THF and 19.5 ml (0.0195 moles) of 1N NaOH was kept under stirring at room temperature (20°-25° C.) for 1.5 hours. The mixture was then diluted with water to 300 ml and slowly acidified with 37% HCl. A solid product precipitated which, after filtration and drying, weighed 3.4 grams and was crystallized from ethanol thus giving 2.3 grams of a compound of formula

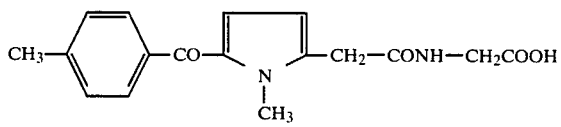

having the following chemico-physical characteristics:
Formula: $C_{17}H_{18}N_2O_4$.
Molecular weight: 314.33.
Melting point: 203°-205° C.
Yield: 57.8% of the theoretical value.
Solubility: soluble in alkali.
Analysis: $C_{17}H_{18}N_2O_4$. Calculated %—C 64.95; H 5.77; N 8.91. Found %—C 64.65; H 5.67; N 8.65.

I.R. Spectrum (nujol): 3275 cm$^{-1}$ (amide NH), 1738 cm$^{-1}$ (C=O carboxyl group), 1625 cm$^{-1}$ (C=O keto and amide groups).

NMR Spectrum (solvent DMSO-d6; standard TMS): δ 2.4 (3H, s, $CH_3$p-toluoyl); 3.7 (2H, s, $CH_2CONH$); 3.8–3.9 (2H, d, $CH_2COOH$); 3.9 (3H, s, $CH_3$—N=); 6.2 (1H, d, proton at 3 in the pyrrole ring); 6.6 (1H, d, proton at 4 in the pyrrole ring); 7.3–7.7 (4H, double doublet, protons of benzene ring); 8.45 (1H, t, NH) ppm.

Mass spectrum:

m/e 314 (M$^{\oplus}$)
m/e 299 [M—$CH_3$]$^{\oplus}$

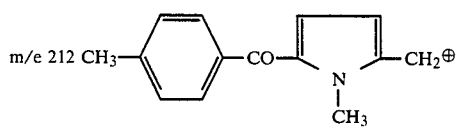
m/e 212

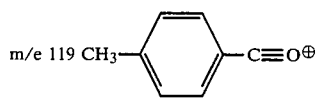
m/e 119

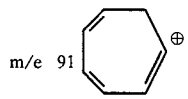
m/e 91

EXAMPLE 3

Preparation of 1-methyl-5-p-toluoylpyrrole-2-acetamidoacetic acid guayacil ester (1-d, see Table II).

To a solution of 1-methyl-5-p-toluoylpyrrole-2-acetamidoacetic acid (1-c) (2.4 grams; 7.64 mmoles) in anhydrous THF (150 ml), a solution of 1,1'-carbonyldiimidazole (1.5 grams; 9.17 mmoles) in anhydrous TFH (70 ml) was added dropwise in 30 minutes. During the addition, a precipitate formed consisting of the imidazolide of the compound (1-c). Upon termination of the addition, the resulting suspension was kept under stirring at room temperature for 1 hour, then a solution of guaiacole (1.4 grams; 9.17 mmoles) in anhydrous THF (30 ml) was added. The suspension was first kept under vigorous stirring at room temperature for 2 hours and then was heated at 70° C. for 0.5 hour. The solvent was removed from the clear solution thus obtained on a hot water bath under vacuum and the oily residue which was obtained was dissolved in ethyl acetate (150 ml). The organic solution was first washed with 1N NaOH (1×100 ml) in order to remove the starting acid and then with a saturated solution of NaCl (3×100 ml) until neutrality was reached. After drying on anhydrous sodium sulphate, the solution was filtered and the solvent was removed from the filtrate by evaporation under vacuum on a hot water bath. In such a way a residue was obtained consisting of the solid product (2.7 grams) which was crystallized from a mixture cyclohexane-benzene (1:1) thus giving 2.3 grams of the compound of formula

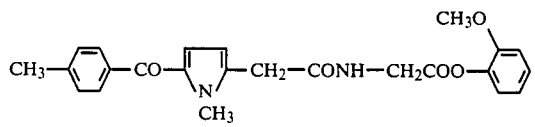

having the following chemico-physical characteristics:
Empirical formula: $C_{24}H_{24}N_2O_5$.
Molecular weight: 420.45.
Melting point: 117°-120° C.
Yield: 71.8% of the theoretical value.
Solubility: soluble in the common organic solvents.
Analysis: $C_{24}H_{24}N_2O_5$. Calculated %—C 68.56; H 5.75; N 6.66. Found %—C 68.35; H 5.85; N 6.97.

I.R. Spectrum (nujol): 3270 cm$^{-1}$ (amide NH), 1770 cm$^{-1}$ (C=O ester), 1650 cm$^{-1}$ (C=O ketone) and 1620 cm$^{-1}$ (C+O amide).

The compounds prepared according to the foregoing procedures and represented by formulas (1), (2) and (3) are illustrated in Tables II and III. For each compound the following data are indicated: molecular weight, melting point, crystallization solvent, yield and reaction time.

The compound (1-c) was obtained by alkaline hydrolysis of the ester (1-b) with the stechiometrical amount of 1N NaOH, as described in details in the example 2, since it was not possible to carry out the direct amidation of 1-methyl-5-p-toluoylpyrrole-2-acetic acid with glycine. The compound (1-d) was obtained by esterification of the acid (1-c) with guaiacole in the presence of a suitable condensing agent as described in detail in example 3.

TABLE II

N—monosubstituted derivatives of 1-methyl-5-p-toluoylpyrrole-2-acetamide

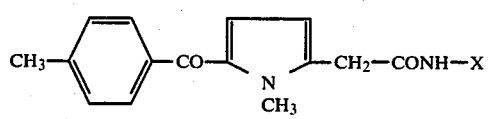
(1)

| Compound | X | Empirical formula | Molecular weight | Melting point °C. | Yield % | Reaction time | Crystallized from |
|---|---|---|---|---|---|---|---|
| 1-a | cyclohexyl | $C_{21}H_{26}N_2O_2$ | 338.43 | 225–226 | 67.6 | 30 min. | ethanol |
| 1-b | —$CH_2COOC_2H_5$ | $C_{19}H_{22}N_2O_4$ | 342.38 | 132–133 | 78.7 | 3 h 30 min | cyclohexane-benzene (1:1) |
| 1-c | —$CH_2COOH$ | $C_{17}H_{18}N_2O_4$ | 314.33 | 203–205 | 57.5 | — | ethanol |
| 1-d | —$CH_2COO$-(2-methoxyphenyl) | $C_{24}H_{24}N_2O_5$ | 420.45 | 117–120 | 71.9 | — | cyclohexane-benzene (1:1) |
| 1-e | —$CH_2CH_2SH$ | $C_{17}H_{20}N_2O_2S$ | 316.35 | 165–169 | 20.0 | 3 h | ethyl acetate |
| 1-f | —$CH(CH_2SH)COOCH_3$ | $C_{19}H_{22}N_2O_4S$ | 374.38 | 122–125 | 89.3** | 3 h | — |
| 1-g | 4-methylpyridin-2-yl | $C_{21}H_{21}N_3O_2$ | 347.40 | 171–172 | 72.0 | 1 h | ethanol |
| 1-h | 4-($COOC_2H_5$)phenyl | $C_{24}H_{24}N_2O_4$ | 404.45 | 183–184 | 45.0 | 30 min. | benzene |
| 1-i | 4-(COOH)phenyl | $C_{22}H_{20}N_2O_4$ | 376.40 | >280 | 53.2 | 2 h | ethanol-N,N—dimethyl-formamide |
| 1-l | 4-(OH)phenyl | $C_{21}H_{20}N_3O_3$ | 348.39 | 231–233 | 50.0 | 2 h | ethanol |
| 1-m | 3-($CF_3$)phenyl | $C_{22}H_{22}F_3N_2O_2$ | 403.20 | 139–141 | 61.7 | 1 h 30 min | carbon-tetrachloride |
| 1-n | 3,5-dimethylphenyl | $C_{23}H_{24}N_2O_2$ | 360.44 | 224–228 | 72.2 | 2 h | ethanol |

TABLE II-continued

N—monosubstituted derivatives of 1-methyl-5-p-toluoylpyrrole-2-acetamide $$CH_3-\phenyl-CO-\pyrrole(N-CH_3)-CH_2-CONH-X \quad (1)$$

| Compound | X | Empirical formula | Molecular weight | Melting point °C. | Yield % | Reaction time | Crystallized from |
|---|---|---|---|---|---|---|---|
| 1-o | —NHCH₂CON⟨NCH₃⟩ | $C_{22}H_{28}N_4O_3$ | 396.48 | 199–201 | 60.0 | 2 h*** | ethanol |

*Calculated after amine addition.
**Calculated on the raw product.
***1 h at room temperature and 1 h at reflux temperature.

TABLE III

N,N—disubstituted derivatives of 1-methyl-5-p-toluoylpyrrole-2-acetamide $$CH_3-\phenyl-CO-\pyrrole(N-CH_3)-CH_2-CON\langle R, R'\rangle \quad (2)$$

$$CH_3-\phenyl-CO-\pyrrole(N-CH_3)-CH_2-CON\langle Z \rangle \quad (3)$$

| Compound | R | R' | Z | Empirical formula | Molecular weight | Melting point °C. | Crystallized from | Yield % | Reaction time* |
|---|---|---|---|---|---|---|---|---|---|
| 2-a | $C_2H_5$ | $C_2H_5$ | — | $C_{19}H_{24}N_2O_2$ | 312.40 | 83–84 | cyclohexane | 80.2 | 30 min. |
| 3-a | — | — | O | $C_{19}H_{22}N_2O_3$ | 326.38 | 137–138 | cyclohexane-benzene (1:1) | 67.4 | 30 min. |
| 3-b | — | — | N—CH₃ | $C_{20}H_{25}N_3O_2$ | 339.42 | 113–117 | cyclohexane-benzene (1:1) | 53.0 | 1 h |

*Calculated after amine addition.

PHARMACOLOGICAL PROPERTIES

The experiments carried out with the N-monosubstituted and N,N-disubstituted derivatives of 1-methyl-5-p-toluoylpyrrole-2-acetamide given in Tables II and III show that these products possess pharmacological properties suitable for therapeutic application in some pathological conditions. The preparations that had been administered via the oral and/or parenteral route, were in suspension of 0.5% carboxymethylcellulose in neutral pH physiological saline solution. In particular the compounds of this invention exhibited an acute inflammatory inhibiting action concomitantly to a marked analgesic action. It has also been demonstrated, as described below, that these derivatives have a considerable antithermic activity, and in vivo tests show good antisecretory and antitussive activity. All these pharmacotherapeutic effects were obtained with doses and administration regimens that did not provoke significant toxic effects. In general the toxicity of these substances is very low and in particular gastrolesions are markedly contained as described in the examples below. Doses, the routes of administration and in general the methods whereby the effects on animals are obtained suggest that these compounds can be useful in human therapy for pathological situations characterized by phlogosis and pain. As an example the experimental data are described below of the activity of some of the compounds under reference compared with that of the dihydrated sodium salt of 1-methyl-5-p-toluoyl-2-acetic acid (TOLMETIN Na2H₂O), at equimolecular doses, and also with that of indomethacin in the antiinflammatory test.

ANTI-INFLAMMATORY ACTIVITY

This effect was evaluated by means of an experimental model reproducing acute inflammation: for this purpose the carrageenin-induced oedema test was employed following the method described by C. A. Winter (J. Pharmac. Exp. Ther. 141: 369, 1963) using a reference substance of known anti-inflammatory activity: indomethacin and tolmetin Na.2H₂O (S. Wong, J. F. Gardocki and T. P. Pruss, J. Pharmac. Exp. Ther. 185(1): 127, 1973).

Albino male Wistar rats weighing 140–160 g were caged for 10 days at 22°±1° C. and given a balanced diet and water ad libitum. Eighteen hours before the experiment the animals were randomized into groups of ten and fasted but with free access to water. Each dose was tested in three groups of rats. Each compound was given either orally, by gavage, or parenterally—intraperitoneal injection—administering as follows:

controls: 0.5% carboxymethylcellulose suspension in physiological saline, 10 ml/kg treated: suspension of the compounds to be tested in the same vehicle and at the same volume (10 ml/kg) used for the controls at the doses specified below.

One hour after administration of the compounds and vehicle, in order to provoke the oedema for determining the protective effect of the substances under examination, each rat received, by subcutaneous injection into the plantar surface of the left paw, 0.1 ml of 1% sterile carrageenin suspension. The changes in the plantar volumes of each animal were determined by the plethysmometric method using a digital water plethysmograph (model 7150-Basile) at 2, 4, 6, 24, 48 and 72 hours after administering the oedema inducing substance. Oedema inhibition was calculated by referring to the plantar surface of the untreated paw and the degree of inflammation in the controls.

Table IV lists the tested compounds, the concentration thereof, routes of administration and relative percentage oedema inhibitions; the data are commented upon at the end of the Table.

and given a balanced diet with free access to water. Twenty-four hours before the experiment the animals were randomized into groups of 10 and fasted for 14 hours but with free access to water. Each dose was tested in 3 groups of rats. Thirty minutes following administration either orally or parenterally of the products to be tested and the vehicle alone (0.5% carboxymethylcellulose in physiological saline) in the control animals, each rat was given 2 ml of a 5% absolute ethanol aqueous solution containing 0.36% of phenyl-p-quinone (Sigma Chemical Company) in order to provoke writhings. Fifteen minutes after administration of phenyl-p-quinone the number of contractions were counted for 20 minutes. The inhibiting effect of the compounds under examination on the abdominal contractions induced by phenyl-p-quinone was calculated by the following formula:

$$\% \text{ protection} = \frac{\text{no. of contractions in controls} - \text{no. of contractions in treated rats}}{\text{no. of contractions in controls}} \times 100$$

Table V lists the tested compounds, doses, routes of administration and their efficacy expressed as percentage of protection, taking into account that phenyl-p-quinone was administered thirty minutes after the compounds.

Table V-a gives the analgesic activity of compounds

TABLE IV

Antiinflammatory activity of N—monosubstituted and N,N—disubstituted derivatives of 1-methyl-5-p-toluoylpyrrole-2-acetamide

| Compounds | Dose mg/Kg | oedema % inhibition per os | | | | | | oedema % inhibition i.p. | | | | | |
|---|---|---|---|---|---|---|---|---|---|---|---|---|---|
| | | 2 h | 4 h | 6 h | 24 h | 48 h | 72 h | 2 h | 4 h | 6 h | 24 h | 48 h | 72 h |
| Vehicle | — | 0.0 | 0.0 | 0.0 | 0.0 | 0.0 | 0.0 | 0.0 | 0.0 | 0.0 | 0.0 | 0.0 | 0.0 |
| Indomethacin | 2.5 | 20.6 | 33.7 | 25.2 | 6.0 | 0.0 | 0.0 | 25.7 | 38.0 | 30.0 | 5.0 | 0.0 | 0.0 |
| " | 5 | 34.3 | 45.9 | 42.1 | 4.2 | 0.0 | 0.0 | 39.0 | 50.1 | 48.0 | 7.0 | 0.0 | 0.0 |
| " | 10 | 66.4 | 53.2 | 51.6 | 20.0 | 6.0 | 0.0 | 70.8 | 66.6 | 65.0 | 16.0 | 0.0 | 0.0 |
| Tolmetin Na.H$_2$O | 10 | 44.8 | 29.2 | 10.2 | 0.0 | 0.0 | 0.0 | 46.0 | 39.1 | 20.0 | 0.0 | 0.0 | 0.0 |
| " | 50 | 48.0 | 55.3 | 55.2 | 0.0 | 0.0 | 0.0 | 53.8 | 60.0 | 58.4 | 0.0 | 0.0 | 0.0 |
| " | 100 | 50.8 | 57.3 | 54.8 | 9.7 | 7.8 | 0.0 | 57.0 | 66.0 | 67.1 | 8.7 | 2.0 | 0.0 |
| 1-c | 25 | 38.6 | 39.1 | 37.2 | 12.1 | 0.0 | 0.0 | 40.0 | 44.8 | 45.0 | 9.0 | 0.0 | 0.0 |
| " | 50 | 51.8 | 58.9 | 60.4 | 18.7 | 0.0 | 0.0 | 55.0 | 64.0 | 65.4 | 20.0 | 8.0 | 0.0 |
| " | 100 | 69.0 | 70.1 | 67.0 | 26.0 | 10.0 | 0.0 | 74.8 | 77.5 | 74.0 | 30.4 | 12.0 | 0.0 |
| 1-d | 2.5 | 50.0 | 34.6 | 23.1 | 0.0 | 0.0 | 0.0 | 52.3 | 37.0 | 26.0 | 14.0 | 0.0 | 0.0 |
| " | 5 | 51.4 | 38.8 | 24.0 | 10.0 | 10.0 | 6.0 | 54.0 | 40.0 | 24.6 | 10.1 | 0.0 | 0.0 |
| " | 10 | 61.5 | 41.2 | 34.9 | 12.6 | 14.0 | 9.0 | 60.0 | 46.9 | 36.7 | 16.5 | 6.3 | 0.0 |
| " | 20 | 62.1 | 48.7 | 32.8 | 26.6 | 25.9 | 3.3 | 65.0 | 50.4 | 48.6 | 23.5 | 9.1 | 8.4 |
| " | 50 | 66.9 | 66.8 | 57.8 | 30.9 | 36.3 | 38.6 | 69.7 | 74.0 | 67.2 | 34.5 | 20.8 | 15.3 |
| " | 100 | 68.0 | 74.0 | 67.5 | 40.3 | 38.0 | 33.0 | 76.5 | 79.5 | 73.4 | 42.4 | 33.0 | 31.6 |
| 1-h | 25 | 28.9 | 30.1 | 29.0 | 8.3 | 0.0 | 0.0 | 30.1 | 27.9 | 29.0 | 13.0 | 0.0 | 0.0 |
| " | 50 | 48.9 | 49.0 | 47.1 | 9.9 | 0.0 | 0.0 | 50.2 | 51.0 | 47.0 | 15.1 | 0.0 | 0.0 |
| " | 100 | 66.9 | 67.1 | 69.0 | 22.0 | 13.0 | 0.0 | 70.1 | 68.9 | 66.0 | 19.0 | 10.0 | 0.0 |
| 1-o | 25 | 37.1 | 42.0 | 44.0 | 12.1 | 0.0 | 0.0 | 39.0 | 37.1 | 36.0 | 11.1 | 0.0 | 0.0 |
| " | 50 | 49.2 | 50.1 | 50.0 | 22.1 | 4.5 | 0.0 | 52.1 | 55.0 | 43.0 | 17.9 | 0.0 | 0.0 |
| " | 100 | 70.1 | 73.4 | 77.5 | 33.5 | 8.6 | 0.0 | 79.1 | 78.0 | 77.3 | 24.1 | 0.0 | 0.0 |
| 3-a | 25 | 27.1 | 29.0 | 32.3 | 7.1 | 0.0 | 0.0 | 28.9 | 32.7 | 34.0 | 10.1 | 0.0 | 0.0 |
| " | 50 | 46.0 | 49.1 | 48.0 | 13.4 | 0.0 | 0.0 | 50.7 | 48.9 | 42.0 | 11.2 | 0.0 | 0.0 |
| " | 100 | 60.0 | 55.2 | 69.7 | 18.1 | 0.0 | 0.0 | 69.8 | 69.0 | 63.0 | 13.1 | 0.0 | 0.0 |
| 3-b | 25 | 28.1 | 33.4 | 30.0 | 10.2 | 0.0 | 0.0 | 33.2 | 36.0 | 30.0 | 10.0 | 0.0 | 0.0 |
| " | 50 | 49.1 | 48.0 | 49.7 | 15.2 | 0.0 | 0.0 | 52.3 | 55.6 | 58.9 | 11.2 | 0.0 | 0.0 |
| " | 100 | 69.7 | 68.0 | 69.0 | 35.0 | 8.9 | 0.0 | 73.4 | 77.1 | 72.9 | 25.6 | 1.4 | 0.0 |

ANALGESIC ACTIVITY

By means of the phenylquinone-induced writhing test described by E. Siegmund (Proc.Soc.Exp.Biol.Med. 95: 729, 1957) the analgesic activity of some of the compounds listed in Tables II and III was evaluated in comparison with the known analgesic activity produced by TOLMETIN Na2H$_2$O, (H. Nakamura and M. Shimizu, Br. J. Pharmacol. 73: 779, 1981). Male Wistar rats weighing 110±5 g were caged for 10 days at 22±1° C.

1-d in comparison with TOLMETIN, taking into account that these compounds were administered via the oral route 1, 2, 4, 6, 8, 16, 24 hours before phenyl-p-quinone.

TABLE V

Analgesic activity of N—monosubstituted and N,N—disubstituted derivatives of 1-methyl-5-p-toluoyl-pyrrole-2-acetamide
(phenyl-p-quinone writhing test)

TABLE V-continued

| Compounds | Dose mg/Kg | % Protection per os | i.p. |
|---|---|---|---|
| Vehicle | — | 0.00 | 0.0 |
| Tolmetin Na.2H2O | 5 | 15.0 | 16.5 |
| " | 10 | 40.0 | 46.2 |
| " | 20 | 62.0 | 69.1 |
| 1-c | 5 | 25.3 | 27.1 |
| " | 10 | 49.0 | 46.3 |
| " | 20 | 85.1 | 82.0 |
| 1-d | 5 | 29.1 | 22.1 |
| " | 10 | 53.4 | 56.0 |
| " | 20 | 80.2 | 87.0 |
| 1-h | 5 | 16.2 | 18.0 |
| " | 10 | 37.9 | 44.0 |
| " | 20 | 70.1 | 79.0 |
| 1-o | 5 | 29.3 | 35.1 |
| " | 10 | 60.4 | 63.9 |
| " | 20 | 86.2 | 87.0 |
| 3-a | 5 | 16.0 | 18.0 |
| " | 10 | 39.0 | 48.0 |
| " | 20 | 65.0 | 76.0 |
| 3-b | 5 | 20.0 | 28.0 |
| " | 10 | 52.0 | 50.0 |
| " | 20 | 78.0 | 80.3 |

Analgesic activity of 1-methyl-5-p-toluoylpyrrole-2-acetamidoacetic acid guaiacyl ester (1-d) and tolmetin Na.2H2O after oral administration at 1, 2, 4, 6, 8, 16, 24 hours before phenyl-quinone administration.

| Compounds | Dose mg/Kg | % Protection | | | | | | |
|---|---|---|---|---|---|---|---|---|
| | | 1 h | 2 h | 4 h | 6 h | 8 h | 16 h | 24 h |
| Vehicle | — | 0.0 | 0.0 | 0.0 | 0.0 | 0.0 | 0.0 | 0.0 |
| Tolmetin Na.2H2O | 10 | 51.8 | 35.5 | 32.0 | 17.2 | 20.2 | 3.0 | 5.0 |
| Tolmetin Na.2H2O | 20 | 79.6 | 78.0 | 50.0 | 45.3 | 40.1 | 8.7 | 4.2 |
| Tolmetin Na.2H2O | 50 | 81.0 | 84.6 | 62.5 | 49.7 | 45.0 | 9.3 | 3.8 |
| 1-d | 10 | 55.7 | 43.3 | 40.1 | 44.0 | 32.0 | 12.1 | 10.0 |
| " | 20 | 78.1 | 80.6 | 70.5 | 66.3 | 71.0 | 23.6 | 25.0 |
| " | 50 | 86.4 | 87.0 | 81.5 | 76.8 | 75.0 | 60.7 | 64.0 |

ANTIPYRETIC ACTIVITY

In order to determine this activity, hyperthermia was induced in albino male Wistar rats weighing 250±10 g by intraperitoneally injecting 10 ml/kg of a 1.5% suspension of dry, purified brewers' yeast (Carlo Erba). The substance used for comparison was TOLMETIN Na.2H2O the antipyretic activity whereof is well known (S. Wong, S. F. Gardocki and T. P. Pruss, J. Pharmac. Exp. Ther. 185(1): 127, 1973). The animals were caged under the same conditions as those described in the preceding tests. Five hours following administration of the yeast those animals with 1.5° C. or more increase in body temperature versus basal values, determined by a rectal probe connected to a YSI thermometer (73 ATP model, Yellow Springs Instrument Company) were selected for the experiment. The animals were then randomized into groups of 10 and the compounds under examination and the vehicle were administered via the oral and parenteral routes testing each dose in two groups. Body temperature was determined at one, two and three hours after administration of the substances. By means of these determinations it was possible to establish the percentage changes in the body temperature of the treated groups compared with the controls which had received the vehicle alone. Table VI lists the tested compounds, doses, routes of administration and % decrease in body temperature.

TABLE VI

Antipyretic activity of N—monosubstituted and N,N—disubstituted derivatives of 1-methyl-5-p-toluoylpyrrole-2-acetamide

| Compounds | Dose mg/Kg | % Temperature decrease | | | | | |
|---|---|---|---|---|---|---|---|
| | | per os | | | i.p. | | |
| | | 1 h | 2 h | 3 h | 1 h | 2 h | 3 h |
| Tolmetin Na.2H2O | 50 | 12.0 | 20.0 | 29.5 | 15.0 | 19.0 | 30.5 |
| " | 75 | 13.0 | 26.0 | 27.0 | 18.0 | 29.0 | 34.0 |
| " | 100 | 18.0 | 30.9 | 47.0 | 28.0 | 39.0 | 51.0 |
| 1-c | 50 | 15.0 | 23.0 | 32.0 | 20.0 | 21.9 | 36.0 |
| " | 75 | 16.5 | 30.7 | 42.1 | 19.0 | 32.6 | 45.2 |
| " | 100 | 27.1 | 31.2 | 57.9 | 35.0 | 49.1 | 65.7 |
| 1-d | 50 | 14.0 | 22.0 | 31.6 | 16.0 | 23.0 | 37.5 |
| " | 75 | 18.5 | 23.4 | 29.1 | 22.1 | 33.4 | 39.8 |
| " | 100 | 22.0 | 42.5 | 59.0 | 28.1 | 37.2 | 60.4 |
| 1-h | 50 | 13.0 | 28.0 | 31.1 | 12.0 | 29.1 | 36.2 |
| " | 75 | 17.0 | 29.1 | 39.4 | 18.0 | 27.2 | 39.4 |
| " | 100 | 21.0 | 35.1 | 51.8 | 23.1 | 39.3 | 60.2 |
| 1-o | 50 | 12.0 | 23.1 | 35.2 | 13.0 | 27.5 | 39.6 |
| " | 75 | 16.0 | 25.2 | 40.2 | 18.0 | 27.0 | 49.6 |
| " | 100 | 29.1 | 33.7 | 59.0 | 30.1 | 45.0 | 62.1 |
| 3-a | 50 | 15.5 | 23.0 | 32.1 | 16.0 | 26.0 | 36.7 |
| " | 75 | 16.2 | 29.1 | 39.4 | 19.0 | 30.2 | 39.4 |
| " | 100 | 22.0 | 29.5 | 56.1 | 21.3 | 36.1 | 58.1 |
| 3-b | 50 | 13.1 | 21.0 | 36.2 | 12.9 | 23.0 | 38.3 |
| " | 75 | 19.0 | 29.1 | 40.6 | 23.4 | 29.0 | 48.5 |
| " | 100 | 27.0 | 35.0 | 59.7 | 32.9 | 39.0 | 60.1 |

ANTISECRETORY ACTIVITY

The experiment was carried out in accordance with the method described by Y.Kasé (Folia Pharmacol. Jap. 73: 605, 1977) for the purpose of investigating whether or not the compounds under examination determine changes in the volume of the mucus secreted by the respiratory airway. Groups of four albino male New Zealand rabbits (mean weight: 2.5 kg) were used for testing each dose per single group. The animals were anaesthetized with urethane (1.1 g/kg b.w.) via the intraperitoneal route and a Y cannula was inserted into the trachea. In order to stimulate mucous secretion a humidifier was connected to the cannula permitting the animals to spontaneously breathe air with 100% humidity at a constant temperature of 39° C. The secreted mucus was collected through another opening in the cannula and measured at three and six hours after administration of the compounds under examination or of the vehicle alone administered in the order of 2 mg/kg (controls). Calculation of the increase or decrease in mucous secretion was based upon the percentage differences between the groups treated with the compounds under examination and the control group. Table VII gives the percentage differences in mucous secretion, and the tested compounds with relative doses and routes of administration.

TABLE VII

Antisecretory activity of N—monosubstituted and N,N—disubstituted derivatives of 1-methyl-5-p-toluoylpyrrole-2-acetamide

| Compounds | Dose mg/Kg | % difference in mucus secretion | | | |
|---|---|---|---|---|---|
| | | per os | | i.p. | |
| | | 3 h | 6 h | 3 h | 6 h |
| Tolmetin Na.2H2O | 50 | +5% | +10% | +3% | +7% |
| " | 75 | 0.0 | +2% | +8% | +10% |
| " | 100 | +5% | 0.0 | +7% | 0.0 |
| 1-c | 50 | 0.0 | +6% | 0.0 | 0.0 |
| " | 75 | −10% | −8% | −12% | −7% |
| " | 100 | −35% | −22% | −37% | −25% |
| 1-d | 50 | 0.0 | 0.0 | −5% | −5% |
| " | 75 | −15% | −10% | −18% | −15% |
| " | 100 | −32% | −27% | −38% | −30% |

TABLE VII-continued
Antisecretory activity of N—monosubstituted and
N,N—disubstituted derivatives of 1-methyl-5-p-
toluoylpyrrole-2-acetamide

| Compounds | Dose mg/Kg | % difference in mucus secretion | | | |
|---|---|---|---|---|---|
| | | per os | | i.p. | |
| | | 3 h | 6 h | 3 h | 6 h |
| 1-h | 50 | −5% | 0.0 | −8% | −3% |
| " | 75 | −19% | −16% | −26% | −20% |
| " | 100 | −39% | −32% | −41% | −38% |
| 3-a | 50 | −7% | −8% | −10% | −7% |
| " | 75 | −15% | −10% | −20% | −18% |
| " | 100 | −32% | −25% | −38% | −29% |
| 3-b | 50 | −9% | −5% | −12% | −10% |
| " | 75 | −18% | −10% | −25% | −22% |
| " | 100 | −36% | −30% | −40% | −36% |

ANTITUSSIVE ACTIVITY

The antitussive effect on albino Guinea-pigs weighing 300 g was evaluated using the method described by Y. Kasé (Selected Pharmacological Testing Methods, p.363, Marcel Dekker Inc., New York, 1968). Each dose was tested in a group of animals with a Y cannula inserted into the trachea. In order to provoke coughing, the mucosa of the tracheal bifurcation was mechanically stimulated by insertion of a wild boar's hair through an opening in the cannula, while the other opening was connected to a kymograph to plot the amplitude and/or frequency. The reduction in the number of coughs was evaluated at one hour after administration of the compounds under examination by following the plottings for twenty minutes and comparing the response of the control animals. Table VIII lists the tested compounds, doses, routes of administration and percentage of coughs.

TABLE VIII
Antitussive activity of N—monosubstituted and
N,N—disubstituted derivatives of 1-methyl-5-p-
toluoylpyrrole-2-acetamide

| Compounds | Dose mg/Kg | % inhibition | | | |
|---|---|---|---|---|---|
| | | per os | | i.p. | |
| | | Amplitude | Frequency | Amplitude | Frequency |
| Tolmetin Na.2H$_2$O | 50 | 0 | 0 | 0 | 0 |
| Tolmetin Na.2H$_2$O | 75 | 7 | 0 | 0 | 10 |
| Tolmetin Na.2H$_2$O | 100 | 5 | 5 | 7 | 10 |
| 1-c | 50 | 12 | 20 | 10 | 25 |
| " | 75 | 20 | 22 | 15 | 27 |
| " | 100 | 38 | 45 | 40 | 51 |
| 1-d | 50 | 10 | 18 | 12 | 15 |
| " | 75 | 22 | 29 | 20 | 36 |
| " | 100 | 30 | 49 | 30 | 45 |
| 1-h | 50 | 13 | 10 | 20 | 18 |
| " | 75 | 22 | 18 | 29 | 35 |
| " | 100 | 40 | 50 | 45 | 53 |
| 3-a | 50 | 15 | 16 | 20 | 15 |
| " | 75 | 30 | 18 | 30 | 16 |
| " | 100 | 35 | 45 | 40 | 56 |
| 3-b | 50 | 18 | 29 | 20 | 28 |
| " | 75 | 30 | 18 | 30 | 20 |
| " | 100 | 45 | 39 | 52 | 40 |

ULCEROGENIC ACTIVITY

Male Wistar rats weighing 180 g were randomized into groups of 10. Three doses of each compound were administered. One group received the vehicle alone (10 ml/kg b.w.). Each dose was given orally for four days consecutively and the rats were sacrificed on the fifth day for necropsy. The ulcerogenic effect was evaluated by the following scale:

Number of Lesions (1) each haemorrhagic point at least 1 mm in diameter was scored as 1 lesion,
(2) haemorrhagic points less than 1 mm in diameter were scored in the following manner:
  (a) 1 to 9=one lesion
  (b) 10 to 19=two lesions
  (c) 20 to 29=three lesions

Severity of Lesions

| | |
|---|---|
| (1) no lesion | 0 |
| (2) gastric mucosal irritation without haemorrhage | 1 |
| (3) haemorrhagic points less than 1 mm in diameter | 2 |
| (4) haemorrhagic points between 1 and 3 mm in diameter | 3 |
| (5) haemorrhagic points larger than 3 mm in diameter | 4 |
| (6) perforations | 5 |

By means of this scale it was possible to obtain the gastric damage index:

$$I = \text{means no. lesions} + \text{mean of severity} + \frac{\% \text{ incidence}}{10}$$

The results are given in Table IX.

TABLE IX
Ulcerogenic ativity of N—monosubstituted and
N,N—disubstituted derivatives of 1-methyl-5-p-
toluoylpyrrole-2-acetamide

| Compounds | Dose mg/Kg | mean no. of lesions | mean severity | % incidence 10 | gastric damage index |
|---|---|---|---|---|---|
| Vehicle | — | 1 | 1 | 6 | 8 |
| Tolmetin Na.2H$_2$O | 50 | 2 | 2 | 7 | 11 |
| Tolmetin Na.2H$_2$O | 100 | 2.5 | 3.5 | 10 | 16 |
| Tolmetin Na.2H$_2$O | 200 | 3 | 4 | 10 | 17 |
| 1-c | 50 | 1 | 1.5 | 7 | 9.5 |
| " | 100 | 2 | 2 | 8 | 12 |
| " | 200 | 2.5 | 2 | 9 | 13.5 |
| 1-d | 50 | 1.5 | 1 | 6 | 8.5 |
| " | 100 | 2 | 1.5 | 9 | 12.5 |
| " | 200 | 2 | 2 | 9 | 13 |
| 1-h | 50 | 1 | 1 | 7 | 9 |
| " | 100 | 1.5 | 1 | 8 | 10.5 |
| " | 200 | 2 | 1.5 | 8 | 11.5 |
| 1-o | 50 | 1 | 1 | 7 | 9 |
| " | 100 | 2 | 1 | 9 | 12 |
| " | 200 | 2 | 2 | 8 | 12 |
| 3-a | 50 | 1 | 1 | 7 | 9 |
| " | 100 | 1.5 | 2 | 8 | 11.5 |
| " | 200 | 1.5 | 2 | 9 | 12.5 |
| 3-b | 50 | 1 | 1 | 7 | 9 |
| " | 100 | 1 | 2 | 7 | 10 |
| " | 200 | 2 | 3 | 8 | 13 |

TOXICITY

Acute toxicity of the compounds under examination was determined in albino male Swiss mice (23±1 g) and male Wistar rats (110 g) via the oral and intraperitoneal routes. Table X lists the LD$_{50}$ values (mg/kg).

TABLE X

Acute toxicity of N—monosubstituted and N,N—disubstituted derivatives of 1-methyl-5-p-toluoyl-pyrrole-2-acetamide

| Compounds | Animal Species | LD$_{50}$ (mg/Kg) per os | i.p. |
|---|---|---|---|
| Tolmetin Na.2H$_2$O | Mice | 899 | 550 |
| | Rats | 914 | 612 |
| 1-c | Mice | 1000 | 700 |
| | Rats | 1300 | 780 |
| 1-d | Mice | >1500 | 1370 |
| | Rats | 1450 | 1100 |
| 1-h | Mice | >2400 | >2000 |
| | Rats | 1800 | 1609 |
| 1-o | Mice | 910 | 590 |
| | Rats | 978 | 700 |
| 3-a | Mice | >2000 | 1500 |
| | Rats | >2400 | 1370 |
| 3-b | Mice | 1200 | 770 |
| | Rats | 1000 | 590 |

The data given in Tables IV–VIII show the considerable pharmaco-therapeutical effect of N-monosubstituted and N,N-disubstituted derivatives of 1-methyl-5-p-toluoyl pyrrole-2-acetamide at the tested doses and in comparison with the control products. Especially as regards anti-inflammatory activity, phlogosis was inhibited for more than twenty-four hours in the carrageenin-induced oedema test. The low toxicity of the above derivatives confers to them a high therapeutical value: in fact it may be observed that the acute toxicity values (Table X) are of several magnitudes higher than those used for reaching pharmacologically active doses. Moreover, it is interesting to observe that the ulcerogenic effect is moderate as regards the number of gastric lesions and their severity (Table IX) contrary to anti-inflammatory agents in general which produce a marked ulcerogenic effect. Administration to healthy animals at the doses and routes used in the experiments did not provoke death in the long- or short-term nor apparent signs of toxic effects. The results given in Tables IV—VIII witness the therapeutical interest of the pharmaceutical compositions of the present invention.

The patients in need of an antiinflammatory, analgesic, antipyretic and antisecretive pharmaceutical composition will be orally or parenterally administered a therapeutically effective amount of a compound of general formula (I).

The dose of compound of general formula (I) orally or parenterally administered will be generally comprised between about 2 and about 15 mg/Kg of body weight/day, although larger or smaller doses can be administered by the attending physician having regard to the age, weight and general conditions of the patient, utilizing sound professional judgement.

In practice, the compounds are orally or parenterally administered in any of the usual pharmaceutical forms which are prepared by conventional procedures well-known to those persons skilled in the pharmaceutical technology. These forms include solid and liquid unit dosage forms such as tablets, capsules, suppositories, solutions, syrups and the like as well as injectable forms, such as sterile solutions for ampoules and phials. Hereinbelow some non-limiting examples of compositions suitable for oral or parenteral administration are given.

| PHARMACEUTICAL COMPOSITIONS | |
|---|---|
| (1) CAPSULE | |
| Each capsule contains: | |
| active principle | 200 mg |
| excipients | |
| starch | 48 mg |
| lactose | 143 mg |
| magnesium stearate | 1.5 mg |
| sodium lauryl sulfate | 0.2 mg |
| (2) INJECTABLE PHIAL (3 ml) | |
| Each phial contains: | |
| active principle | 175 mg |
| excipients | |
| propylene glycol | 250 mg |
| sodium metabisulfite | 9 mg |
| sodium hydroxide | 3.6 mg |
| lidocaine hydrochloride | 10 mg |
| sterile bidistilled water balance to | 3 ml |
| (3) SUPPOSITORY | |
| Each suppository contains: | |
| active principle | 200 mg |
| excipients | |
| mixture of triglycerides of vegetal saturated fatty acids | 750 mg |
| polysorbate | 250 mg |

What is claimed is:
1. A compound having the formula

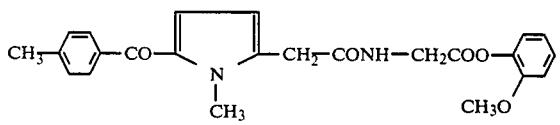

* * * * *